United States Patent [19]

Denton

[11] Patent Number: 5,666,194
[45] Date of Patent: Sep. 9, 1997

[54] APPARATUS FOR DETECTING MARKING MATERIAL

[75] Inventor: Gary A. Denton, Lexington, Ky.

[73] Assignee: Xerox Corporation, Stamford, Conn.

[21] Appl. No.: 655,587

[22] Filed: May 30, 1996

[51] Int. Cl.$^6$ .......................... G01N 21/55; G03G 21/00
[52] U.S. Cl. .................. 356/72; 356/448; 356/445; 399/9; 399/53; 399/74
[58] Field of Search ............... 356/72, 71, 445, 356/446, 434, 448, 504; 355/246, 208, 245, 251, 203, 259, 326, 327, 271–276; 346/153.1, 157, 159; 430/42, 48

[56] References Cited

U.S. PATENT DOCUMENTS

| | | | |
|---|---|---|---|
| 4,974,024 | 11/1990 | Bares et al. | 355/246 |
| 4,989,985 | 2/1991 | Hubble, III et al. | 356/445 |
| 5,053,822 | 10/1991 | Butler | 355/246 |
| 5,078,497 | 1/1992 | Borton et al. | 356/446 |
| 5,081,491 | 1/1992 | Lux et al. | 355/208 |
| 5,083,161 | 1/1992 | Borton et al. | 355/208 |
| 5,204,699 | 4/1993 | Birnbaum et al. | 346/160 |
| 5,436,705 | 7/1995 | Raj | 355/246 |

*Primary Examiner*—Frank G. Font
*Assistant Examiner*—Michael P. Stafira
*Attorney, Agent, or Firm*—H. Fleischer; J. E. Beck; R. Zibelli

[57] ABSTRACT

An apparatus which detects a mass of marking material developed on a test patch recorded on a photoconductive surface. The apparatus includes a densitometer, a capacitor sensor and a controller. The densitometer is spaced from and adjacent to the photoconductive surface. The capacitor sensor is also positioned adjacent to the photoconductive surface and spaced therefrom. In operation, the densitometer generates a first signal proportional to the specular component of the total reflectivity of the material deposited on the test patch developed on the photoconductive surface. The capacitor sensor generates a second signal proportional to the mass of material developed on the test patch recorded on the surface. In response to these signals, the controller generates a first control signal as a function of the first signal received from the densitometer in response to the mass of material deposited on the test patch being less than a preselected mass. When the mass deposited on the test patch is greater than the preselected mass, the controller generates a second control signal as a function of the second signal received from the capacitor sensor. In this way, a continuous signal is transmitted from the controller independent of the color of the material developed on the test patch.

14 Claims, 7 Drawing Sheets

APPARATUS FOR DETECTING MARKING MATERIAL

This invention relates generally to an electrophotographic printing machine, and more particularly concerns an apparatus for detecting a mass of marking material developed on a photoconductive surface.

In an electrophotographic printing machine, the photoconductive member is charged to a substantially uniform potential to sensitize the surface thereof. The charged portion of the photoconductive member is exposed to a light image of an original document being reproduced. Exposure of the charged photoconductive member selectively dissipates the charge thereon in the irradiated areas. This records an electrostatic latent image on the photoconductive member corresponding to the informational area contained within the original document being reproduced. After the electrostatic latent image is recorded on the photoconductive member, the latent image is developed by bringing marking or toner particles into contact therewith. This forms a powder image on the photoconductive member which is subsequently transferred to a copy sheet. The copy sheet is heated to permanently affix the marking particles thereto in image configuration.

Various types of development systems have previously been employed. These systems utilize two component developer mixes or single component developer mixes. Typical two component developer mixes employed are well known in the art, and generally comprise dyed or color thermoplastic particles, known in the art as toner particles, which are mixed with coarser carrier granules, such as ferromagnetic granules. The toner particles and carrier granules are selected such that the toner particles acquire the appropriate charge relative to the electrostatic latent image recorded on the photoconductive surface. When the developer mix is brought into contact with the charged photoconductive surface, the greater attractive force of the electrostatic latent image recorded thereon causes the toner particles to transfer from the carrier granules and adhere to the electrostatic latent image.

Multicolor electrophotograhic printing is substantially identical to the foregoing process of black and white printing. However, rather than forming a single latent image on the photoconductive surface, successive latent images corresponding to different colors are recorded thereon. Each single color electrostatic latent image is developed with toner particles color complimentary thereto. This process is repeated a plurality of cycles for differently colored images and their respective complimentary colored toner particles. Each single color toner powder image is transferred to the copy sheet in superimposed registration with the prior toner powder image. This creates a multi-layered toner powder image on the copy sheet. Thereafter, the multi-layered toner powder image is permanently affixed to the copy sheet creating a color copy. While we have hereinbefore described a multi-pass, multi-transfer color electrophotographic printing machine, variations thereof are well known in the art. For example, multiple different color toner powder images may be developed on the photoconductive member and transferred simultaneously to the copy sheet. This is referred to in the art as a multipass single transfer color electrophotographic printing machine. Alternatively, successive different color toner powder images may be deposited in superimposed registration with one another on the photoconductive member during a single pass and transferred to the copy sheet during that single pass. This type of color electrophotographic printing machine is known as a single pass, single transfer color electrophotographic printing machine. Finally, the toner powder images may be transferred to an intermediate member such as an intermediate transfer belt and then, subsequently, transferred to the copy sheet for fusing thereto.

In all of the foregoing variations and types of electrophotographic printing machines, the developer material employed may be dry as in the case of toner particles and carrier granules or a liquid as in the case of a mixture of toner particles in a carrier liquid.

Hereinafter when the term marking material is utilized, it is intended to cover both dry and liquid developer materials.

It is evident that in printing machines of this type, toner is depleted from the developer material. As the concentration of toner decreases, the density of the resultant copy degrades in order to maintain the copies being reproduced at a specified minimum density, it is necessary to regulate the concentration of toner in the developer material. This is achieved by a closed loop servo system which regulates developability. Hereinbefore, various types of densitometers have been utilized to detect the mass of developed material on the photoconductive surface. Densitometers have been developed which measure the mass of developed material of both black and color toners by monitoring the specular and diffuse reflectivity thereof. For black and color toners, the specular signal provides a fairly reliable measurement of the developed mass below about 0.35 milligrams/centimeters$^2$. The diffuse densitometer signal may also be utilized to provide destimates of the developed mass for color toners above about 0.4 milligrams per centimeter$^2$, if they are calibrated against the specular signals using a lower developed mass where the specular signals have acceptable signal to noise ratios. However, black toner patches produce such low diffuse signals that only the specular signal is usable for developed mass measurements. This prevents process control schemes from using black patches with the desired developed mass values. This problem has forced the process control strategy to extrapolate the developed mass from 90% area coverage half tone patches and/or from low mass patches that are readable by the densitometer. Thus, it is desirable to be capable of having a system for measuring developed mass on the photoconductive surface for all ranges without the need to extrapolate. Various approaches have been used to measure density and to control the parameters within the printing machine. The following disclosures appear to be relevant:

U.S. Pat. No. 4,989,985

Patentee: Hubble, III et al.

Issued: Feb. 5, 1991

U.S. Pat. No. 5,078,497

Patentee: Borton et al.

Issued: Jan. 7, 1992

U.S. Pat. No. 5,083,161

Patentee: Borton et al.

Issued: Jan. 21, 1992

The relevant portions of the foregoing patents may be briefly summarized as follows:

U.S. Pat. No. 4,989,985 discloses an infrared densitometer which measures the reduction in the specular component of reflectivity as marking particles are progressively deposited on a moving photoconductive belt. Collimated light rays are projected onto the marking particles. The light rays reflected from the marking particles are collected and directed onto a photodiode array. The photodiode array generates electrical signals proportional to the total flux and diffuse component of the total flex of the reflected light rays. Circuitry compares the electrical signals and determines the difference therebetween to generate an electrical signal proportional to the specular component of the total flux of the reflected light rays.

U.S. Pat. No. 5,078,497 describes a densitometer which measures the reduction in the specular component of the reflectivity of a portion of a surface having a liquid deposited thereon. Collimated light rays, in the visible spectrum, are projected onto the portion of the surface having the liquid thereon. The light rays reflected from the liquid are collected and directed onto a photodiode array. The photodiode array generates electrical signals proportional to the total flux and the diffuse component of the total flux of the reflected light rays. Circuitry compares the electrical signals and determines the difference therebetween to generate an electrical signal proportional to the specular component of the total flux of the reflected light rays.

U.S. Pat. No 5,083,161 discloses an infrared densitometer which measures the reflectivity of a selected region of a moving photoconductive belt covered at least partially with marking particles. Collimated light rays are projected onto the selected region of the moving photoconductive member with or without marking particles thereon. The light rays reflected from the selected region of the moving photoconductive member are collected and directed onto a photodiode array. The photodiode array generates electrical signals proportional to the diffuse component of the total reflectivity of the selected region of the photoconductive member with and without marking particles thereon. Circuitry determines a control signal as a function of the difference in electrical signals.

Pursuant to the features of the present invention, there is provided an apparatus for detecting a mass of marking material developed on a surface. The apparatus includes a densitometer, in communication with the surface, for generating a first signal proportional to the specular component of the total reflectivity of the marking material developed on the surface. A capacitor sensor, in communication with the surface, generates a second signal proportional to the mass of marking material developed on the surface. A controller, associated with the densitometer and the capacitor, generates a first control signal as a function of the first signal in response to the mass of marking material being less than a preselected mass and a second control signal as a function of the second signal in response to the mass of marking material being greater than the preselected mass.

In accordance with another aspect of the present invention, there is provided a printing machine of the type in which a mass of marking material developed on a photoconductive surface is detected. The improved printing machine includes a densitometer, in communication with the photoconductive surface, for generating a first signal proportional to the specular component of the total reflectivity of the marking material developed on the photoconductive surface. A capacitor sensor, in communication with the photoconductive surface, generates a second signal proportional to the mass of marking material developed on the surface. A controller, associated with the densitometer and a capacitor, generates a first control signal as a function of the first signal in response to the mass of marking material being less than a preselected mass and a second control signal as a function of the second signal in response to the mass of marking material being greater than the preselected mass.

Other aspects of the present invention will become apparent as following description proceeds and upon reference to the drawings, in which.

While the present invention will hereinafter be described in connection with a preferred embodiment thereof, it will be understood that it is not intended to limit the invention to that embodiment. On the contrary, it is intended to cover all alternatives, modifications and equivalents as may be included within the spirit and scope of the invention as defined by the appended claims.

Figure 1:
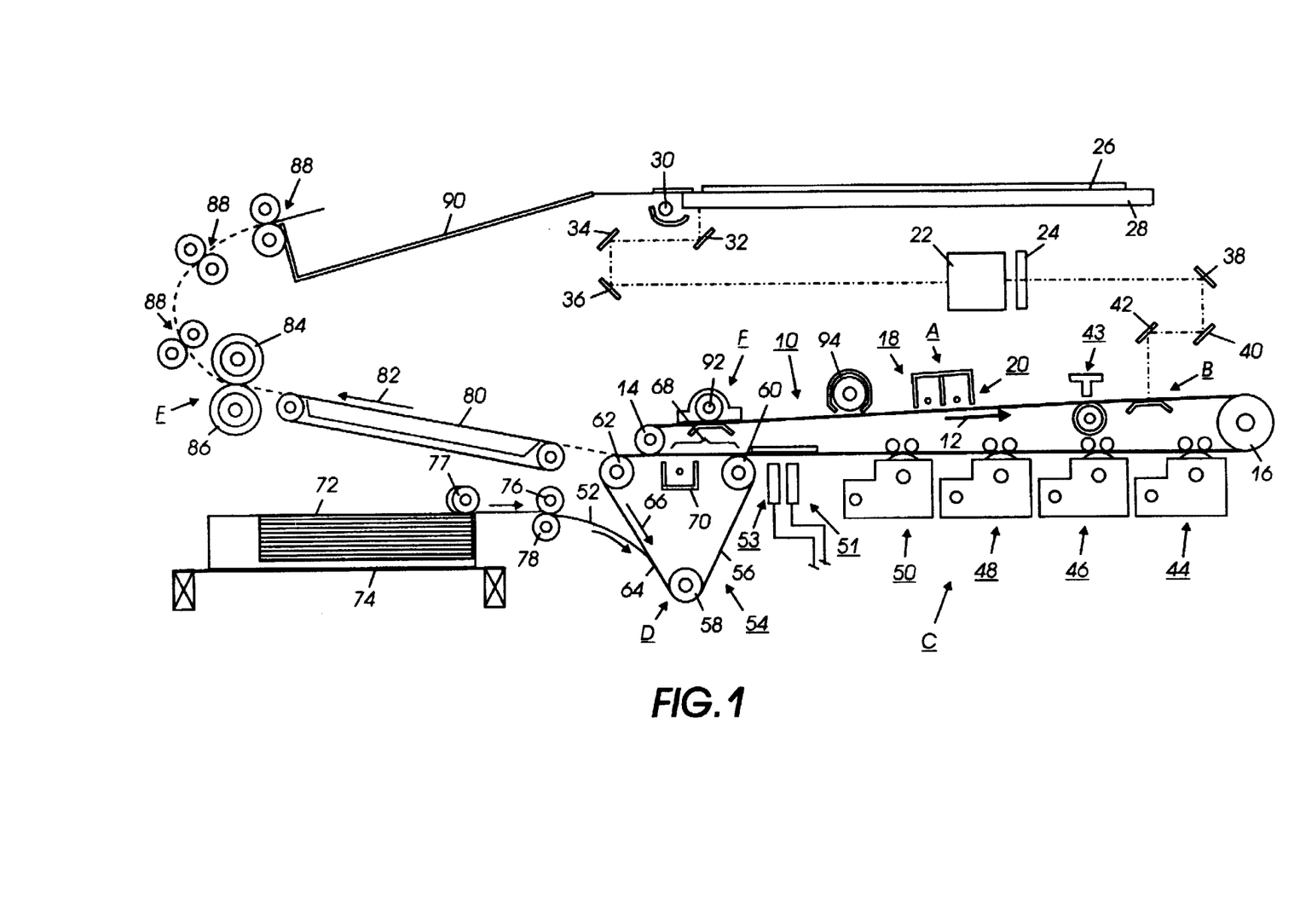
FIG. 1 is a schematic elevational view depicting an electrophotographic printing machine incorporating the apparatus of the present invention therein.

For a general understanding of the features of the present invention, reference is made to the drawings. In the drawings, like reference numerals have been used throughout to designate identical elements. FIG. 1 schematically depicts the various components of an illustrative electrophotographic printing machine incorporating the apparatus of the present invention therein. It will become evident from the following discussion that the apparatus of the present invention is equally well suited for use in a wide variety of printing machines and is not necessarily limited in this application to the particular printing machine shown herein.

Inasmuch as the art of electrophotographic printing is well known, the various processing stations employed in the FIG. I printing machine will be shown hereinafter schematically and their operation described briefly with reference thereto.

As shown in FIG. 1, the electrophotographic printing machine employs a photoconductive belt 10. Preferably, the photoconductive belt 10 is made from a photoconductive material coated on a grounding layer which, in turn, is coated on an anticurl backing layer. The photoconductive material is made from a transport layer coated on generator layer. The transport layer transports positive charges from the generator layer. The interface layer is coated on the grounding layer. The transport layer contains small molecules of di-m-tolydihenylbipenyldiamine dispersed in a polycarbonate. The generation layer is made from trigonal selenium. The grounding layer is made from titanium coated Mylar. The grounding layer is very thin and allows light to pass therethrough. Other suitable, photoconductive materials, grounding layers, and anti-curl backing layers may also be employed. Belt 10 moves in the direction of arrow 12 to advance successive portions of the photoconductive surface sequentially through the various processing stations disposed about the path of movement thereof. Belt, 10 is entrained about idler roller 14 and drive roller 16. Idler roll 14 is mounted rotatably so as to rotate with belt 10. Drive roller 16 is rotated by a motor coupled thereto by suitable means such as a drive belt. As roller 16 rotates, it advances belt 10 in the direction of arrow 12.

Initially, a portion of the photoconductive belt 10 passes through charging station A. At charging station A, two corona generating devices, indicated generally by the reference numerals 18 and 20 charge photoconductive belt 10 to a relatively high, substantially uniform potential.

Next, the charged photoconductive surface is advanced to exposure station B. Exposure station B includes a moving lens system, generally designated by the reference numeral 22, and a color filter mechanism, shown generally by the reference numeral 24. An original document 26 is supported stationarily upon a transparent viewing platen. Successive incremental areas of the original document are illuminated by a moving lamp assembly, shown generally by the reference numeral 30. Mirrors 32, 34 and 36 reflect the light rays through lens 22. Lens 22 is adapted to scan successive areas of illumination of platen 28. The light rays from lens 22 are reflected by mirrors 38, 40 and 42 to be focused the charged portion of photoconductive belt 10. In this way, a flowing light image of the original document is produced on photoconductive belt 10 in a non-distorted manner. During exposure, filter mechanism 24 interposes select color filters into the optical light path of lens 28. The color filters operate on the light rays passing through the lens to record an electrostatic latent image on the photoconductive belt corresponding to a specific color of the light image of the original document. Exposure station B also includes a test area generator, indicated generally by the reference numeral 43, comprising a light source to project a test light image onto the charged portion of the photoconductive surface in the inter-image region, i.e. the region between successive electrostatic latent images recorded on photoconductive belt 10, to record a test area. The test area, as well as the electrostatic latent image recorded on the photoconductive surface of belt 10 are developed with toner particles at the development station.

One skilled in the art will appreciate that a raster input scanner (RIS) associated with a raster output scanner (ROS) may be used instead of a light lens system for a copier and a ROS in communication with a data source, such as a computer, may be used for a printer.

After the electrostatic latent image and test area have been recorded on photoconductive belt, belt 10 advances them to development station C. Development station C includes four individual developer units generally indicated by the reference numerals 44, 46, 48 and 50. The developer units advance a developer material of carrier and toner into contact with the photoconductive surface. Developer units 44, 46 and 48, respectively, apply toner of a specific color which corresponds to the compliment of the specific color separated electrostatic latent recorded on the photoconductive surface. The color of the toner is adapted to absorb light within a preselected spectral region of the electromagnetic wave spectrum corresponding to the wavelength of light transmitted through the filter. For example, an electrostatic latent image formed by passing the light through a green filter will record the red and blue regions of the spectrum as areas of relatively high charged density on photoconductive belt 10, while the green light rays will pass through the filter and cause the charge density on the photoconductive belt 10 to be reduced to voltage level ineffective for development. The charged areas are then made visible by having developer unit 44 applying green absorbing (magenta) toner onto the electrostatic latent image recorded on the photoconductive belt. Similarly, a blue separation is developed by developer unit 46 with yellow toner while a red separation is developed by developer unit 48 with cyan toner. Developer unit 50 contains black toner and is used to develop those areas in black. The developed mass in the test area passes beneath the infrared densitometer, indicated generally by the reference numeral 51. Densitometer 51 is positioned adjacent the photoconductive surface of belt 10 to generate electrical signals proportional to the developed toner mass of the test area. The detailed structure of densitometer 51 will be described hereinafter with reference to FIG. 3 through 5, inclusive. Next, the developed toner mass of the test area passes beneath a capacitor sensor, indicated generally by the reference numeral 53. Capacitor sensor 53 is positioned adjacent the photoconductive surface of belt 10 to also generate electrical signals proportional to the developed toner mass of the test area. The detailed structure of capacitor sensor 53 will be described hereinafter with reference to FIGS. 6 and 7.

After development, the toner image is advanced to transfer station D where it is transferred to a sheet of support material 52, such as plain paper, amongst others. At transfer station D, the sheet transport apparatus, indicated generally by the reference numeral 54, moves sheet 52 into contact with the photoconductive belt 10. Sheet transport 54 has a pair of spaced belts 56 entrained about three rolls, 58, 60 and 62. A gripper 64 extends between belts 56 and moves in unison therewith. Sheet 52 is advanced from a stack of sheets 72 disposed on tray 74. Feed roll 77 advances the uppermost sheet from stack 72 into a nip defined by forwarding rollers 76 and 78. Forwarding rollers 76 and 78 advance sheet 52 to transport 54. Sheet 52 is advanced by forwarding roller 76 and 78 in synchronism with the movement of gripper 64. In this way, the leading edge of sheet 52 arrives at a preselected position to be received by the open gripper 64. The gripper than closes securing the sheets thereto for movement therewith in a recirculating path. As the belts move in the direction of arrow 66, sheet 52 moves into contact with the photoconductive belt, in synchronism with the toner image developed thereon, at transfer zone 68. A corona generating device 70 sprays ions onto the backside of the sheet so as to charge the sheet to the proper magnitude and polarity for attracting the toner image from photoconductive belt 10 thereto. Sheet 52 remains secure to gripper 64 so as to move in a recirculating path for a plurality of cycles. In this way, different color toner images are transferred to sheet 52 in superimposed registration with one another. The aforementioned steps of charging, exposing, developing and transferring are repeated a plurality of cycles to form a multi-color copy of a colored original document.

After the last transfer operation, gripper 64 open and release sheet 52. Conveyor 80 transports sheet 52 in the direction of arrow 82 to fusing station E. At fusing station E, the transferred image is permanently fused to sheet 52. Fusing station E includes a heated fuser roller 84 and pressure roll 86. Sheet 52 passes through the nip defined by fuser roller 84 and pressure roller 86. The toner image contacts fuser roller 84 so as to be affixed to sheet 52. Thereafter, sheet 52 is advanced by forwarding roll pairs 88 to catch tray 90 for subsequent removal therefrom by the machine operator.

Figure 2:
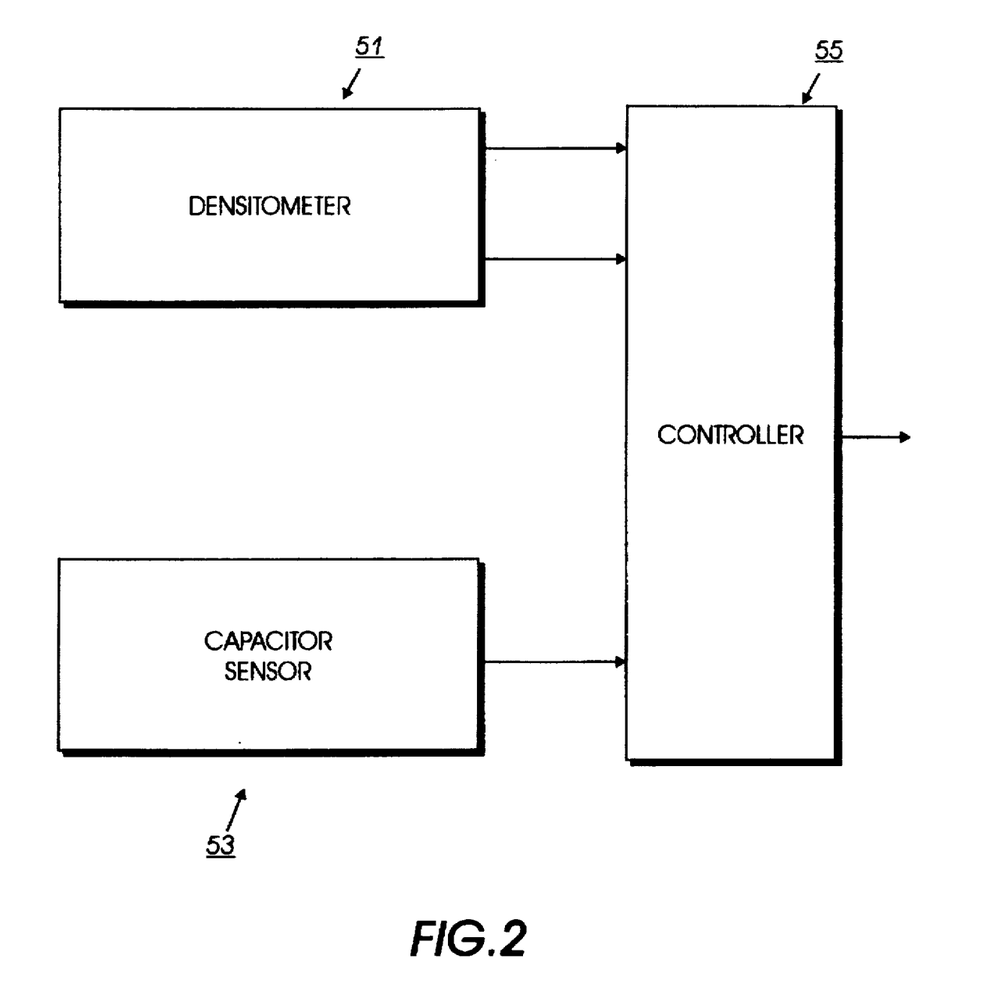
FIG. 2 is a block diagram showing the apparatus of the present invention coupled to a control system.

The last processing station in the direction of movement of belt 10, as indicated by arrow 12, is cleaning station F. A rotatably mounted fibrous brush 92 is positioned in cleaning station F and maintained in contact with photoconductive belt 10 to remove residual toner particles remaining after the transfer operation. Thereafter, lamp 94 illuminates photoconductive 10 to remove any residual charge remaining thereon prior to the start of the next successive cycle Referring now to FIG. 2 there is shown the apparatus for detecting a mass of toner materials developed on the testpatch. As shown in FIG. 2, densitometer 51 transmits two signals to controller 55. The first signal from densitometer 51 is proportional to the specular component of the total reflectivity of the toner mass developed on the test patch on photoconductive belt 10. The second signal generated by densitometer 51 is proportional to the diffused component of the total reflectivity of the toner mass developed on the test patch of the photoconductive belt 10. Capacitor sensor 53 generates a third signal proportional to the toner mass developed on the test patch of photoconductive belt 10. Controller 55 receives the signals from densitometer 51 and capacitor 53. In response to the first signal received from densitometer 51 and the mass of toner material being less than a preselected mass, controller 55 generates a first control signal. In response to the mass of the toner material deposited on the test patch recorded on photoconductive belt 10 being greater than the preselected mass, controller 55 generates a second control signal as a function of the third signal from capacitor sensor 53. Thus, in this mode of operation, controller 55 generates a control signal as a function of the measured specular component of the total reflectivity as determined by densitometer 51 when the mass of toner material developed on the test patch recorded on photoconductive belt 10 is less than a preselected mass. When the mass of toner material developed on the test patch recorded on photoconductive belt 10 is greater than the preselected mass, controller 55 generates a control signal as a function of the signal received from capacitor sensor 53. In an alternative mode of operation, densitomer 51 generates a third signal proportional to the diffuse component of the total reflectivity of the toner material developed on the test patch of photoconductive belt 10. Controller 55 generates a third control signal for non-black toner material as a function of the third signal received from densitometer 51 when the mass of toner material deposited on the test patch is greater than the preselected mass. In this mode of operation, the second control signal from controller 55 is a capacitive measurement of the black toner material deposited on the test patch with the third control signal being a diffuse reflective measurement of the non-black toner material deposited on the test patch. The first signal from densitometer 51 corresponding to the specular component of the total reflectivity of the mass of toner material deposited on the test patch recorded on the photoconductive belt 10, is used to calibrate capacitor sensor 53 when the mass of toner material developed on the test patch is less than the preselected mass. When the mass of toner material deposited on the test patch is greater than the preselected mass, the third signal from densitometer² 51 calibrates capacitor sensor 53. The preselected mass is about 0.4 milligrams/centimeter² for toner particles. The preselected mass may be lower than 0.4 milligrams/centimeter² for a liquid developer material.

Figure 3:
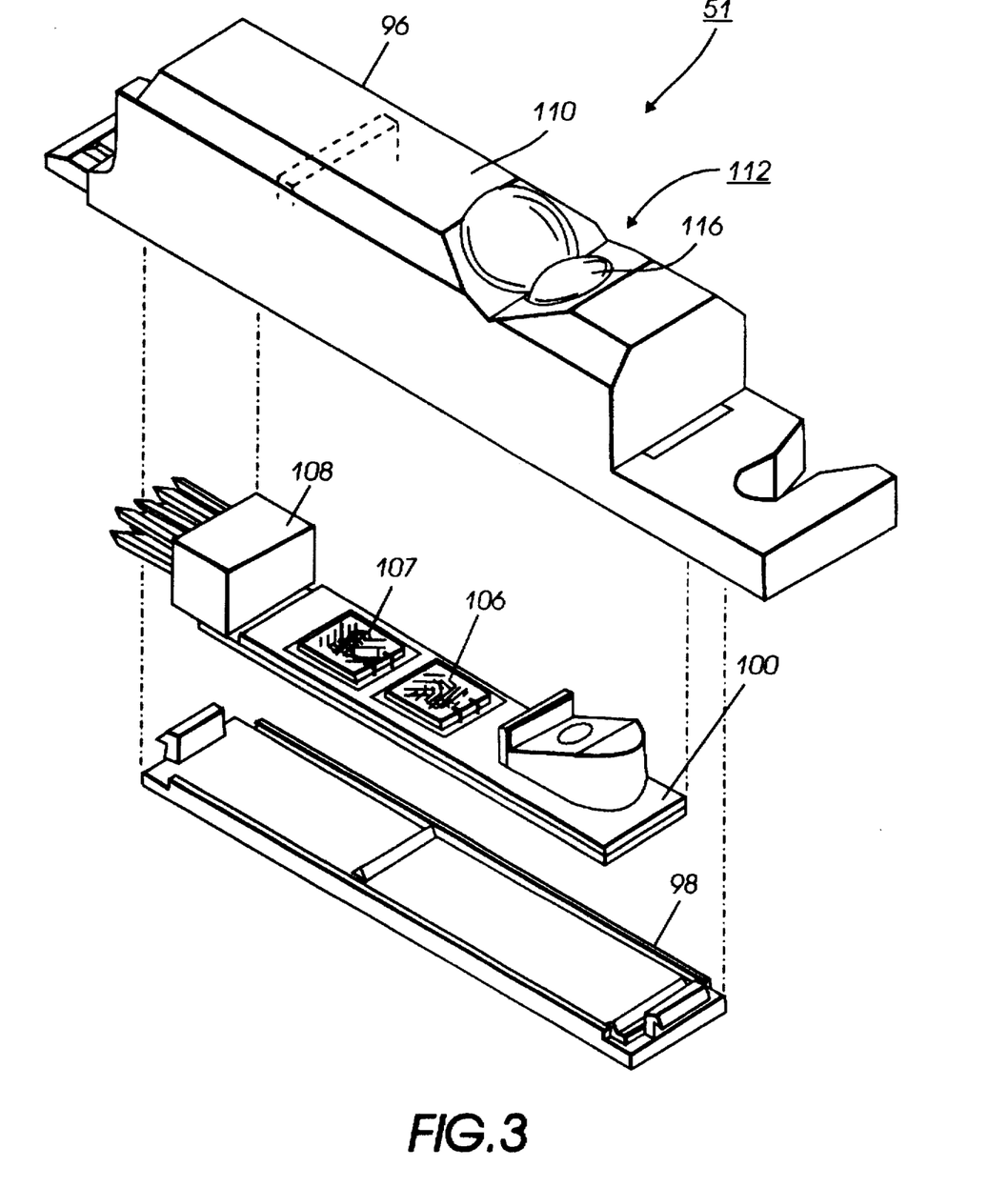
FIG. 3 is a schematic, perspective view showing the densitometer used in the FIG. 1 printing machine.
Figure 4:
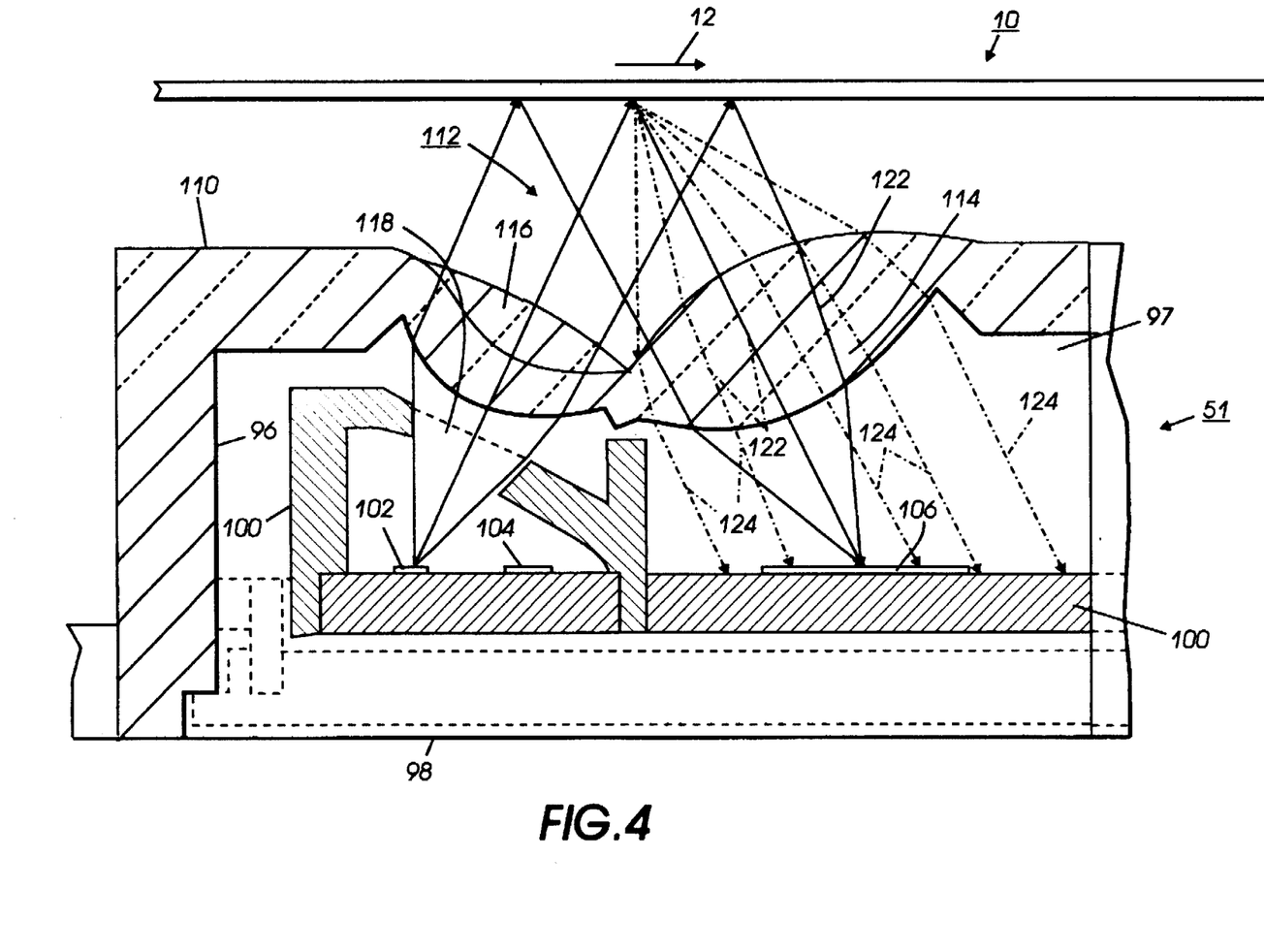
FIG. 4 is fragmentary, sectional elevational view of the FIG. 3 densitometer.
Figure 5:
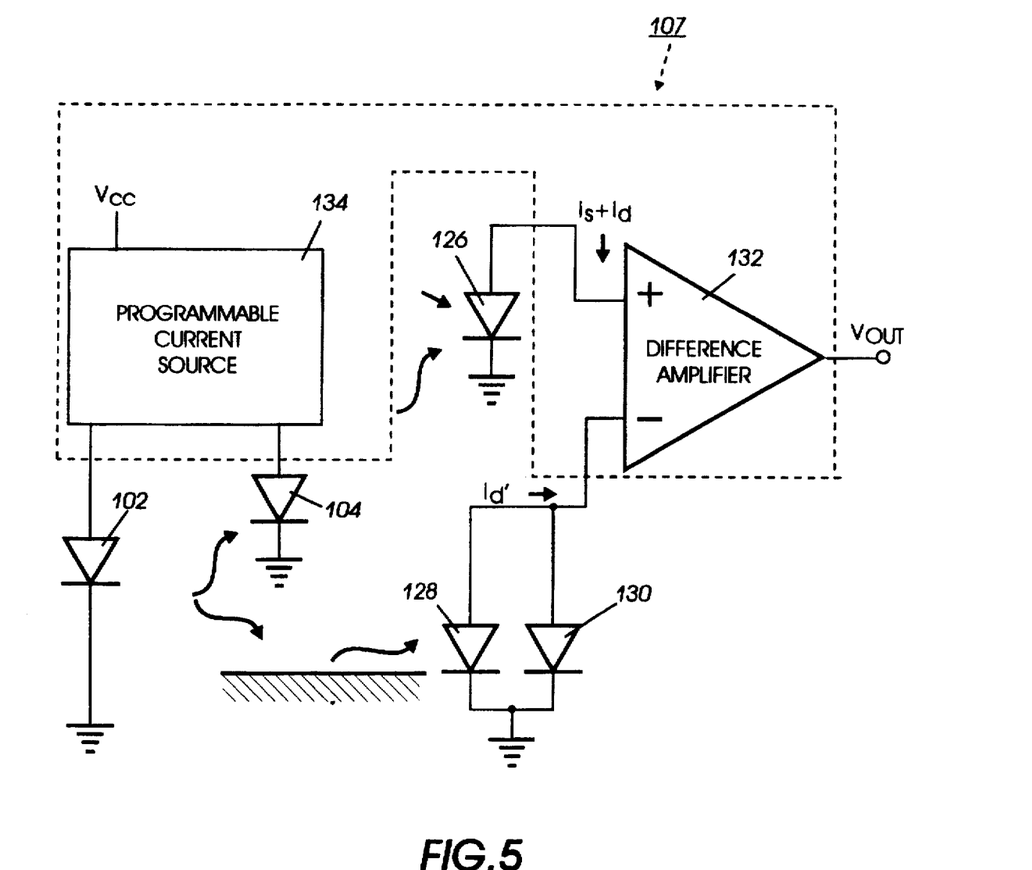
FIG. 5 is a block diagram of the control logic associated with the FIG. 3 densitometer.

Referring now to FIGS. 3 and 4, there is shown infrared densitometer 51 in greater detail. Densitometer 51 includes a generally rectangularly shaped molded housing 96 made preferably from an acrylic material or any other suitable optically transparent material. Housing 96 defines a chamber 97. A cover 98 encloses the bottom of housing 96. A printed circuit wiring board 100 is mounted between cover 98 and housing 96 in chamber 97. Printed circuit board 100 supports a suitable light emitting diode (LED) 102 for providing light rays to illuminate the toner material adhering to the photoconductive surface of belt 10 in the area of the test patch. A control photodiode 104 and photodiode array 106 are also mounted on printed circuit board 100. Connector 108 is also mounted on printer circuit board 100. An integrated circuit chip indicated generally by the reference numeral 107 is electrically connected to LED 102, photodiode 104 and photodiode array 106 to provide a drive current to LED 102 and to process the signals from photodiode 104 and photodiode array 106. The top surface 110 of housing 96 defines a V-shaped recess, generally indicated by the reference numeral 112. One surface of the V-shaped recess 112 supports a condenser lens 116 which is an integral collimating lens. The other surface of the V-shaped recess 112 supports another condenser lens 114 which is integral collector lens. LED 102 generates near infrared light rays which are transmitted through an aperture 118 in cavity 120 onto condenser lens 116. Condenser lens 116 collimates the light rays and focuses the light rays onto the toner material deposited on the test patch recorded on the photoconductive surface of belt 10. Photodiode 104 is positioned to receive a portion of the LED radiant flux reflected from the walls of cavity 120. The output signal from photodiode 104 is compared with a reference signal and the resultant error signal used to regulate the input current to LED 102 to compensate for LED aging and thermal affects. The light rays reflected from the toner material are collected by condenser lens 114 and directed onto the surface of photodiode array 106. The specular component of the reflected light rays or flux, as shown by arrows 122, is focused on a small spot on the surface of the central segment of photodiode array 106. The diffuse components of the reflected light rays or flux, as shown by arrows 124, flood the entire surface of photodiode array 106. The total reflected light rays or flux includes a specular component and a diffuse component of the reflected light rays or flux. A central photodiode generates an electrical signal proportional to the total reflected flux including the diffuse component and specular component thereof. Edge photodiodes are positioned to receive only the diffuse component of the reflected light rays or flux transmitted through the condenser lens 116. The electrical signal generated by the edge photodiodes is proportional to the diffuse component of the reflected light rays or flux. Subtraction of the combined electrical signals of the photodiodes from the electrical signal from the central photodiode yields a resultant electrical signal proportional to the specular component of the light rays or flux reflected from the toner material. A block diagram showing the integrated circuit 107 used to measure the specular component of the light rays is shown in FIG. 5. As shown in FIG. 5, central photodiode 126 generates an electrical signal proportional to the sum of the specular and diffuse components of the light rays. Central photodoide 126 is electrically connected to difference amplifier 132. The electrical output signals from photodiode 128 and 130 are proportional to the diffuse component of the light rays. Photodiodes 128 and 130 are electrically connected to difference amplifier 132 as well. The electrical signals from photodiodes 128 and 130 are combined and transmitted to difference amplifier 132. The voltage output from difference amplifier 132 is proportional only to the specular component of the current output. The electrical signal from control photodiode 104 is transmitted through suitable circuitry to generate a voltage output which regulates current source 134. The current source energizes LED 102. In this way, a feedback loop is formed for driving LED 102 to provide a relatively constant output. Thus, if the signal from the photodiode changes the output from current source 134 is suitably adjusted to maintain a relatively constant light output from LED 102. Further details of densitometer 51 and the associate circuitry may be found U.S. Pat. No. 4,989,985 issued Hubble, III et al. on Feb. 5, 1991, the relevant portions thereof being hereby incorporated into the present application.

Figure 6:
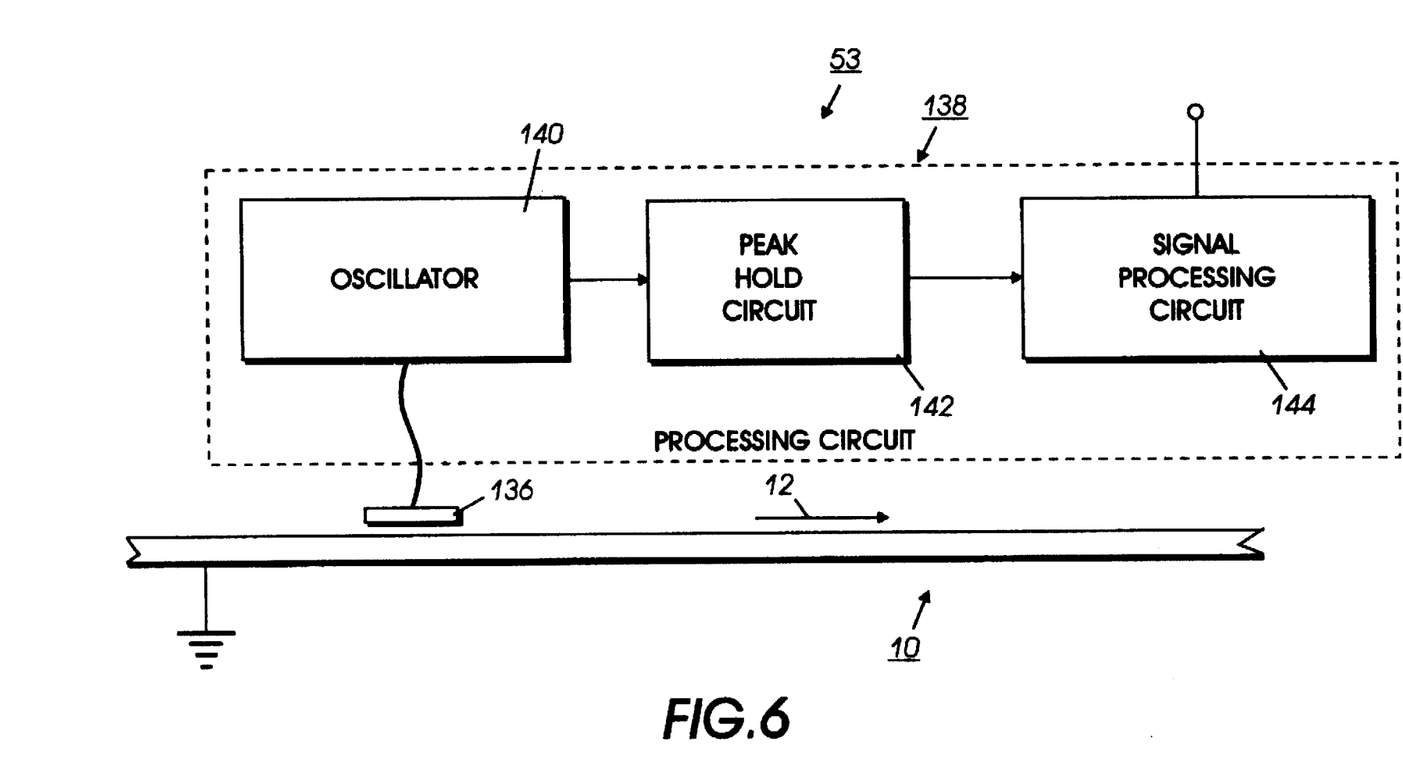
FIG. 6 is a block diagram of the control logic associated with the capacitor sensor.

Turning now to FIG. 6, there is shown capacitor sensor 53. As depicted therein, capacitor sensor 53 includes an aluminum probe 136 positioned adjacent photoconductive belt 10 and spaced therefrom. Aluminum probe 136 is preferably about 0.5 centimeters by 0.5 centimeters by 2 centimeters. The 2 centimeter or long dimension is placed perpendicular to the direction of movement of photoconductive belt 10 as indicated by arrow 12. The test patch is about one inch square. Thus, by positioning the short dimension parallel to the process direction, quick responses are obtained for perturbation, passing under the sensor. The surface area of the aluminum probe controls signal strength. However, larger surface areas average larger sensed areas which reduce the response time. The electronic circuitry, indicated generally by the reference numeral 138, is coupled to the aluminum probe 136. Electronic 138 include an oscillator circuit 140, a peak hold circuit 142 and a signal processing circuit 144. Oscillator 140 is a square wave oscillator operating at 40 Hz with peak hold circuitry 142 being tuned to that frequency. The signal processing circuit 144 takes the output from peak hold circuit 142, subtracts an offset and amplifies the result. The output signal generated by the signal processing circuit 44 is a measure of the change in capacitance between probe 136 and the surface of photoconductive belt 10. The capacitance changes are caused by differences in the electrical permitivity between air and the toner material deposited on the test patch recorded on photoconductive belt 10. The output voltage from the signal processing circuit 144 is inversely proportional to the capacitance.

Figure 7:
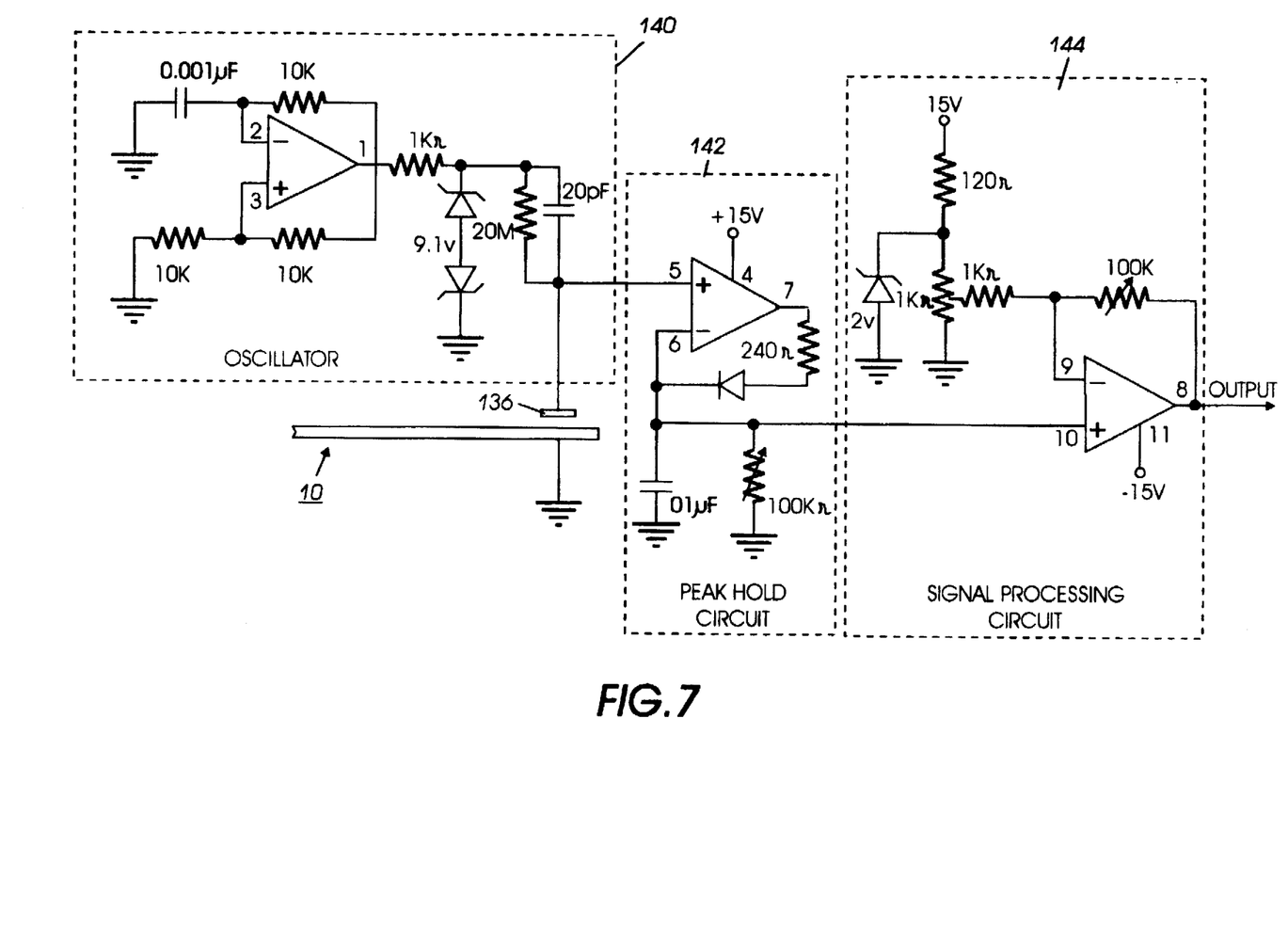
FIG. 7 shows the details of FIG. 6 circuitry.

Referring now to FIG. 7, there is shown the detailed elements of oscillator circuit 140, peak hold circuit 142 and signal processing circuit 44. As shown in FIG. 7, oscillator circuit 140 includes a 0.001 microfarad capacitor connected in parallel with a 10K resistor to an amplifier. Also connected to these input ports are 10K resistors. The output from the amplifier is transmitted through a 1K ohm resistor and then through 9.1 volt diodes connected in parallel with a 20M ohm resistor and 20 pico farad capacitor. The 20M ohm resistance and 20 peak or ferret capacitor are connected to aluminum probe 136 and the positive input of an amplifier. The negative input of the amplifier is connected to the output of the amplifier through a 240 ohm resistor and a diode which is also connected to a 0.1 micro farad connected in parallel with a variable 100K ohm resistor to form the peak hold circuit 142. The output from the peak hold circuit 142 is transmitted to the input of an amplifier of signal processing circuit 144. The negative input to the amplifier is connected to a 1K ohm resistor, a variable 1K ohm resistor and a 120 ohm resistor driven from a 15 volt source. A center tap is connected to a pair of diodes. The output from the amplifier is fed back to the input on the negative turn roll through a variable 100K ohm resistor. The output from signal processing circuit 144 corresponds to the change incapacitance.

In recapitulation, the apparatus of the present invention continually detects the mass of toner developed on a test patch recorded on a photoconductive surface. In one mode of operation, a densitometer generates a signal proportional to the specular component of the total reflectivity of the developed mass of toner on the test patch and a diffuse signal corresponding thereto. A capacitor sensor also generates a signal proportional to the mass of toner material developed on the test patch. A controller receives these signals and processes them such that a first control signal is generated as a function of the specular signal in response to the mass of the toner material deposited on the test patch being less than about 0.4 milligrams per centimeter$^2$. In one mode of operation, the control generates a second control signal as a function of the signal from a capacitor sensor when the mass of toner material deposited on the test patch is greater than 0.4 milligrams per centimeter$^2$. Alternatively, the control signal generates a third control signal for non-black marking material as a function the diffused signal received from the densitometer when the mass of toner material deposited on the test patch is greater than 0.4 milligrams per centimeter$^2$. In this mode of operation, the controller generates a second control signal as a function of the signal received from the capacitor sensor to indicate the mass of black toner material deposited on the test patch. Hence, a continuous signal is generated for both non-black toner material and black toner material.

It is, therefore, evident that there has been provided in accordance with the present invention, an apparatus that fully satisfies the aims and advantages hereinbefore set forth. While this invention has been described in conjunction with specific embodiments thereof, it is evident that many alternatives, modifications and variations will be apparent to those skilled in the art. Accordingly, it is intended to embrace all such alternatives, modifications and variations as fall within the spirit and broad scope of the appended claims.

I claim:

1. An apparatus for detecting a mass of marking material developed on a surface, including:
   - a densitometer, in communication with the surface, for generating a first signal proportional to the specular component of the total reflectivity of the marking material developed on the surface;
   - a capacitor sensor, in communication with the surface, for generating a second signal proportional to the mass of marking material developed on the surface; and
   - a controller, associated with said densitometer and said capacitor, for generating a first control signal as a function of the first signal in response to the mass of marking material being less than a preselected mass and a second control signal as a function of the second signal in response to the mass of marking material being greater than the preselected mass.

2. An apparatus for detecting a mass of marking material developed on a surface, including:
   - a densitometer, in communication with the surface, for generating a first signal proportional to the specular component of the total reflectivity of the marking material developed on the surface;
   - a capacitor sensor, in communication with the surface, for generating a second signal proportional to the mass of marking material developed on the surface;
   - a controller, associated with said densitometer and said capacitor, for generating a first control signal as a function of the first signal in response to the mass of marking material being less than a preselected mass and a second control signal as a function of the second signal in response to the mass of marking material being greater than the preselected mass, said densitometer generates a third signal proportional to the defuse component of the total reflectivity of the marking material developed on the surface, said controller generating a third control signal for non-black marking material as a function of the third signal in response to the mass of marking material being greater than the preselected mass with the second control signal being for black marking material.

3. An apparatus according to claim 2, wherein the first signal from said densitometer calibrates said capacitor sensor in response to the mass of marking material developed on the surface being less than the preselected mass.

4. An apparatus according to claim 3, wherein the third signal from said densitometer calibrates said capacitor sensor in response to the mass of marking material developed on the surface being greater than the preselected mass.

5. An apparatus according to claim 2, wherein the marking material includes particles and the preselected mass is about 0.4 milligrams/centimeters$^2$.

6. An apparatus according to claim 5, wherein said capacitor sensor includes:

a probe positioned adjacent to the surface; and processing circuitry, coupled to said probe, for generating the second signal as a function of a change in capacitance between the surface and said probe.

7. An apparatus according to claim 6, wherein said densitometer includes:

means for determining the total reflectivity of the mass of marking material developed on the surface;

means for determining the diffuse component of the total reflectivity of the mass of marking material developed on the surface; and means for determining the specular component of the total reflectivity of the mass of marking material as a function of the difference between the determined total reflectivity of the mass of marking material and the diffuse component of the total reflectivity of the mass of marking material developed on the surface.

8. A printing machine of the type in which a mass of marking material developed on a photoconductive surface is detected, wherein the improvement includes:

a densitometer, in communication with the photoconductive surface, for generating a first signal proportional to the specular component of the total reflectivity of the marking material developed on the photoconductive surface;

a capacitor sensor, in communication with the photoconductive surface, for generating a second signal proportional to the mass of marking material developed on the surface; and a controller, associated with said densitometer and said capacitor, for generating a first control signal as a function of the first signal in response to the mass of marking material being less than a preselected mass and a second control signal as a function of the second signal in response to the mass of marking material being greater than the preselected mass.

9. A printing machine of the type in which a mass of marking material developed on a photoconductive surface is detected, wherein the improvement includes:

a densitometer, in communication with the photoconductive surface, for generating a first signal proportional to the specular component of the total reflectivity of the marking material developed on the photoconductive surface;

a capacitor sensor, in communication with the photoconductive surface for generating a second signal proportional to the mass of marking material developed on the surface;

a controller, associated with said densitometer and said capacitor, for generating a first control signal as a function of the first signal in response to the mass of marking material being less than a preselected mass and a second control signal as a function of the second signal in response to the mass of marking material being greater than the preselected mass, said densitometer generates a third signal proportional to the diffuse component of the total reflectivity of the marking material developed on the photoconductive surface, said controller generating a third control signal for non-black marking material as a function of the third signal in response to the mass of marking material being greater than the preselected mass with the second control signal being for black marking material.

10. A printing machine according to claim 9, wherein the first signal from said densitometer calibrates said capacitor sensor in response to the mass of marking material developed on the photoconductive surface being less than the preselected mass.

11. A printing machine according to claim 10, wherein the third signal from said densitometer calibrates said capacitor sensor in response to the mass of marking material developed on the photoconductive surface being greater than the preselected mass.

12. A printing machine according to claim 9, wherein the marking material includes particles and the preselected mass is about 0.4 milligrams/centimeters$^2$.

13. A printing machine according to claim 12, wherein said capacitor sensor includes:

a probe positioned adjacent to the surface; and processing circuitry, coupled to said probe, for generating the second signal as a function of a change in capacitance between the surface and said probe.

14. A printing machine according to claim 13, wherein said densitometer includes:

means for determining the total reflectivity of the mass of marking material developed on the photoconductive surface;

means for determining the diffuse component of the total reflectivity of the mass of marking material developed on the photoconductive surface; and means for determining the specular component of the total reflectivity of the mass of marking material as a function of the difference between the determined total reflectivity of the mass of marking material and the diffuse component of the total reflectivity of the mass of marking material developed on the photoconductive surface.

* * * * *